US008475796B2

(12) United States Patent
Hamilton et al.

(10) Patent No.: US 8,475,796 B2
(45) Date of Patent: Jul. 2, 2013

(54) METHOD OF TREATING PAIN USING AN ANTAGONIST OF GM-CSF

(75) Inventors: John Allan Hamilton, Carlton (AU); Andrew David Cook, Carlton (AU)

(73) Assignee: University of Melbourne, Carlton/Victoria (AU)

( * ) Notice: Subject to any disclaimer, the term of this patent is extended or adjusted under 35 U.S.C. 154(b) by 0 days.

(21) Appl. No.: 13/140,839

(22) PCT Filed: Dec. 21, 2009

(86) PCT No.: PCT/AU2009/001671
§ 371 (c)(1),
(2), (4) Date: Aug. 4, 2011

(87) PCT Pub. No.: WO2010/071923
PCT Pub. Date: Jul. 1, 2010

(65) Prior Publication Data
US 2011/0287027 A1 Nov. 24, 2011

Related U.S. Application Data

(60) Provisional application No. 61/139,687, filed on Dec. 22, 2008, provisional application No. 61/164,491, filed on Mar. 30, 2009.

(51) Int. Cl.
*A61K 39/395* (2006.01)
*C07K 16/24* (2006.01)

(52) U.S. Cl.
USPC .......... 424/145.1; 424/130.1; 530/387.1; 530/388.23

(58) Field of Classification Search
None
See application file for complete search history.

(56) References Cited

U.S. PATENT DOCUMENTS

| | | | |
|---|---|---|---|
| 5,475,087 A * | 12/1995 | Seelig et al. | 530/326 |
| 5,747,032 A | 5/1998 | Metcalf | |
| 5,932,704 A * | 8/1999 | Jubinsky | 530/388.22 |
| 7,427,401 B2 | 9/2008 | Lopez | |
| 7,455,836 B2 * | 11/2008 | Hamilton et al. | 424/139.1 |
| 7,741,450 B2 | 6/2010 | Sass | |
| 7,935,795 B2 | 5/2011 | Nakajima | |
| 2002/0141994 A1 | 10/2002 | Devalaraja et al. | |
| 2004/0241755 A1 | 12/2004 | Buckbinder | |
| 2006/0067938 A1 | 3/2006 | Daouti | |
| 2007/0197434 A1 | 8/2007 | Nakao | |
| 2007/0243225 A1 | 10/2007 | McKay | |
| 2008/0227789 A1 | 9/2008 | Goff | |
| 2008/0292641 A1 | 11/2008 | Sass | |
| 2008/0311111 A1 | 12/2008 | Drew | |

FOREIGN PATENT DOCUMENTS

| | | |
|---|---|---|
| WO | 9102063 | 2/1991 |
| WO | 9409149 | 4/1994 |
| WO | 02/100387 | 12/2002 |
| WO | 03068920 | 8/2003 |
| WO | 2005105844 | 11/2005 |
| WO | 2006111353 | 10/2006 |
| WO | 2006122797 | 11/2006 |
| WO | 2007092939 | 8/2007 |
| WO | 2007110631 | 10/2007 |
| WO | 2008064321 | 5/2008 |
| WO | 2008141391 | 11/2008 |
| WO | 2009038760 | 3/2009 |
| WO | 2009062238 | 5/2009 |
| WO | 2009064399 | 5/2009 |
| WO | 2009134805 | 11/2009 |
| WO | 2010124163 | 10/2010 |

OTHER PUBLICATIONS

Matthias Schweizerhof, et al. "Hematopoietic colony—stimulating factors mediate tumor-nerve interactions and bone cancer pain", Nature Medicine Advance Online Publication, Received Nov. 19, 2008; accepted May 5, 2009; published online Jun. 7, 2009; doi:10.1038/nm.1976.
Campbell et al., "Human articular cartilage and chondrocytes produce hemopoietic colony-stimulating factors in culture in response to IL-11," J. Immunology, Aug. 15, 1991, 147(4):1238-1246.
Campbell, I.K. et al., The colony-stimulating factors and collagen-induced arthritis: exacerbation of disease by M-CSF and G-CSF and requirement for endogenous M-CSF, Journal of Leukocyte Biology, vol. 68, Jul. 2000, 144-150.
Firestein, G.S. et al., Cytokines in Chronic Inflammatory Arthritis, The Rockefeller University Press vol. 168, Nov. 1988, 1573-1586.
Hercus et al., 'Specific human granulocyte-macrophage colony-stimulating factor antagonists,' PNAS, Jun. 1994, 91:5838-5842.
Kinne et al., 'Macrophages in rheumatoid arthritis,' Arthritis Research, 2000, 2 (3):189-202.
Leizer et al., 'Cytokine Regulation of Colony-Stimulating Factor Production in Cultured Human Synovial Fibroblasts: I. Induction of GM-CSF and G-CSF Production by Interleukin-1 and Tumor Necrosis Factor,' Blood, Nov. 15, 1990, 76(10):1989-1996.
Metcalf, Donald, 'The Florey Lecture, 1991: The Colony-Stimulating Factors: Discovery to Clinical Use,' Philosophical Transactions: Biological Sciences, Jul. 29, 1991, 333(1266):147-173.
Williamson et al., "The detection and initial characterization of colony-stimulating factors in synovial fluid," Clin. Exp. Immunol., 1988, 72:67-73.
Alvaro-Gracia et al., "Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-a," J Immunol., May 15, 1991, 146(10):33653371.

(Continued)

*Primary Examiner* — Christine J Saoud
*Assistant Examiner* — Jon M Lockard

(57) ABSTRACT

The present invention relates generally to a method for the treatment and prophylaxis of pain. In accordance with the present invention, it is proposed that antagonists of GM-CSF are effective in the treatment of pain. Antagonists of GM-CSF include, but are not limited to, antibodies which are specific for GM-CSF or the GM-CSF receptor. The present invention further provides transgenic animals, such as a GM-CSF knock-out mouse, useful for testing antagonists in certain disease models.

7 Claims, 6 Drawing Sheets

OTHER PUBLICATIONS

Campbell et al., "Granulocyte-macrophage colony stimulating factor exacerbates collagen induced arthritis in mice," Ann. Rheum. Dis., 1997, 56:364-368.

Cebon et al., "Granulocyte-macrophage stimulating factor from human lymphocytes," J. Biol. Chem., Mar. 15, 1990, 265(8):4483-4491.

Chen et al., 'Selection and Analysis of an Optimized Anti-VEGF Antibody: Crystal Structure of an Affinity-matured Fab in Complex with Antigen,' J. Mol. Biol., 1999, 283:865-881.

Clark et al., "The human hematopoietic colony-stimulating factors," Science, Jun. 5, 1987, 236:1229-1237.

Cook et al., "Blockade of collagen-induced arthritis post-onset by antibody to granulocyte-macrophage colony-stimulating factor (GM-CSF): requirement for GM-CSF in the effector phase of disease," Arthritis Research, 2001, 3:293-298.

de Vries et al., "Flare-up of rheumatoid arthritis during GM-CSF treatment after chemotherapy," Lancet, Aug. 24, 1991, 338:517-518.

Hamilton, J.A., "Rheumatoid arthritis: opposing actions of hemopoietic growth factors and slow acting anti-rheumatic drugs," Lancet, Aug. 28, 1993, 342:536-539.

Hamilton, J.A., "GM-CSF in inflammation and autoimmunity," Trends Immunol., Aug. 2002, 23(8):403408.

Haworth et al., "Expression of granulocyte-macrophage colony-stimulating factor in rheumatoid arthritis: regulation by tumor necrosis factor-a," Eur. J. Immunol., 1991, 21:2575-2579.

Kitamura et al., "Idiopathic pulmonary alveolar proteinosis as an autoimmune disease with neutralizing antibody against granulocyte/macrophage colony-stimulating factor," J.Exp. Med., Sep. 20, 1999, 190(6):875-880.

Krinner et al., "A human monoclonal IgG1 potently neutralizing the pro-inflammatory cytokine GM-CSF," Molecular Immunology, Feb. 2007, 44 (5):916-925.

McQualter et al., "Granulocyte macrophage colony-stimulating factor: a new putative therapeutic target in multiple sclerosis," J. Exp. Med., Oct. 1, 2001, 194(7):873-881.

Meager et al., "Spontaneously occurring neutralizing antibodies against granulocyte-macrophage colony-stimulating factor in patients with autoimmune disease," Immunology, 1999, 97:526-532.

Mulherin et al., "Synovial tissue macrophage populations and articular damage in rheumatoid arthritis.," Arthritis & Rheumatism, Jan. 1996, 39(1):115-124.

Olver et al., "A phase I study of the GM-CSF antagonist E21R," Cancer Chemother. Pharmacol., 2002, 50:171-178.

Xu et al., "Cytokines in chronic inflammatory arthritis. II. Granulocyte-macrophage colony-stimulating factor in rheumatoid synovial effusions," J. Clin. Invest., Mar. 1989, 83:876-882.

Plater-Zyberk C. et al. GM-CSF Neutralisation Suppresses Inflammation and Protects Cartilage in Acute Streptococcal Cell Wall Arthritis of Mice // Ann Rheum Dis. Apr. 2007; 66(4): 452-457, Published online Oct. 4, 2006. doi: 10.1136/ard.2006.057182 PMCID: PMC1856054.

* cited by examiner

Results are expressed as the mean ± SEM.

\* p=0.04, \*\* p=0.04, \*\*\* p=0.02, \*\*\*\*p=0.005. Unpaired t-test.

SEQUENCE LISTING

```
<160> NUMBER OF SEQ ID NOS: 46

<210> SEQ ID NO 1
<211> LENGTH: 140
<212> TYPE: PRT
<213> ORGANISM: artificial
<220> FEATURE:
<223> OTHER INFORMATION: amino acid sequence of heavy chain variable
      region

<400> SEQUENCE: 1

Met Glu Leu Ile Met Leu Phe Leu Leu Ser Gly Thr Ala Gly Val His
1               5                   10                  15
```

```
Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
            35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu
65                  70                  75                  80

Phe Lys Asn Arg Ala Thr Leu Thr Val Asp Lys Ser Ser Thr Ala
                85                  90                  95

Tyr Met Glu Leu Arg Ser Leu Thr Ser Asp Asp Ser Ala Val Tyr Tyr
                100                 105                 110

Cys Ala Arg Arg Asp Arg Phe Pro Tyr Tyr Phe Asp Tyr Trp Gly Gln
            115                 120                 125

Gly Thr Thr Leu Arg Val Ser Ser Val Ser Gly Ser
    130                 135                 140
```

<210> SEQ ID NO 2
<211> LENGTH: 150
<212> TYPE: PRT
<213> ORGANISM: artificial
<220> FEATURE:
<223> OTHER INFORMATION: amino acid sequence of light chain variable region

<400> SEQUENCE: 2

```
Met Gly Phe Lys Met Glu Ser Gln Ile Gln Val Phe Val Tyr Met Leu
1               5                   10                  15

Leu Trp Leu Ser Gly Val Asp Gly Asp Ile Val Met Ile Gln Ser Gln
            20                  25                  30

Lys Phe Val Ser Thr Ser Val Gly Asp Arg Val Asn Ile Thr Cys Lys
            35                  40                  45

Ala Ser Gln Asn Val Gly Ser Asn Val Ala Trp Leu Gln Gln Lys Pro
    50                  55                  60

Gly Gln Ser Pro Lys Thr Leu Ile Tyr Ser Ala Ser Tyr Arg Ser Gly
65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
                100                 105                 110

Gln Gln Phe Asn Arg Ser Pro Leu Thr Phe Gly Ser Gly Thr Lys Leu
            115                 120                 125

Glu Leu Lys Arg Ala Asp Ala Ala Pro Thr Val Ser Ile Phe Pro Pro
    130                 135                 140

Ser Ser Lys Gly Glu Phe
145                 150
```

<210> SEQ ID NO 3
<211> LENGTH: 117
<212> TYPE: PRT
<213> ORGANISM: artificial
<220> FEATURE:
<223> OTHER INFORMATION: amino acid sequence of heavy chain variable region

<400> SEQUENCE: 3

```
Gln Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
        20                  25                  30

Trp Met Asn Trp Val Arg Gln Ala Pro Gly Lys Gly Leu Glu Trp Val
            35                  40                  45

Ser Gly Ile Glu Asn Lys Tyr Ala Gly Gly Ala Thr Tyr Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
            115
```

<210> SEQ ID NO 4
<211> LENGTH: 105
<212> TYPE: PRT
<213> ORGANISM: artificial
<220> FEATURE:
<223> OTHER INFORMATION: amino acid sequence of light chain variable
      region

<400> SEQUENCE: 4

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
            35                  40                  45

Lys Lys Arg Pro Ser Gly Ile Pro Glu Arg Phe Ser Gly Ser Asn Ser
 50                  55                  60

Gly Asn Thr Ala Thr Leu Thr Ile Ser Gly Thr Gln Ala Glu Asp Glu
 65                  70                  75                  80

Ala Asp Tyr Tyr Cys Ser Ala Trp Gly Lys Gly Met Val Phe Gly Gly
                85                  90                  95

Gly Thr Lys Leu Thr Val Leu Gly Gln
            100                 105
```

<210> SEQ ID NO 5
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 5

```
Ser Gly Leu Ile Phe Asp Tyr Trp Leu Asp
 1               5                  10
```

<210> SEQ ID NO 6
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 6

```
Ser Gly Leu Ile Ile Asp Ala Leu Ser Pro
 1               5                  10
```

```
<210> SEQ ID NO 7
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 7

Thr Ser Leu Met Ser Ile Tyr Phe Asp Tyr
1               5                   10

<210> SEQ ID NO 8
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 8

Ser Gly Leu Leu Phe Leu Tyr Phe Asp Tyr
1               5                   10

<210> SEQ ID NO 9
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 9

Ser Gly Leu Ile Asn Leu Gly Met His Pro
1               5                   10

<210> SEQ ID NO 10
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 10

Ser Gly Leu Ile Phe Asp Ala Leu Arg Asp
1               5                   10

<210> SEQ ID NO 11
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 11

Ser Gly Leu Ile Phe Asp Lys Leu Thr Ser
1               5                   10

<210> SEQ ID NO 12
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)
```

-continued

```
<400> SEQUENCE: 12

Ser Gly Leu Ile Asn Leu His Phe Asp Thr
1               5                   10

<210> SEQ ID NO 13
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 13

Ser Thr His Phe Ser Ala Tyr Phe Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 14

Ser Gly Leu Ile Met Asp Lys Leu Asp Asn
1               5                   10

<210> SEQ ID NO 15
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 15

Ser Gly Leu Ile Ile Asp Asn Leu Asn Pro
1               5                   10

<210> SEQ ID NO 16
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 16

Ser Gly Leu Ile Ala Val Tyr Phe Asp Tyr
1               5                   10

<210> SEQ ID NO 17
<211> LENGTH: 5
<212> TYPE: PRT
<213> ORGANISM: artificial
<220> FEATURE:
<223> OTHER INFORMATION: amino acid sequence of heavy CDR1 (H-CDR1)

<400> SEQUENCE: 17

Asp Tyr Leu Leu His
1               5

<210> SEQ ID NO 18
<211> LENGTH: 17
<212> TYPE: PRT
<213> ORGANISM: artificial
<220> FEATURE:
```

-continued

<223> OTHER INFORMATION: amino acid sequence of heavy CDR2 (H-CDR2)

<400> SEQUENCE: 18

Trp Leu Asn Pro Tyr Ser Gly Asp Thr Asn Tyr Ala Gln Lys Phe Gln
1               5                   10                  15
Gly

<210> SEQ ID NO 19
<211> LENGTH: 11
<212> TYPE: PRT
<213> ORGANISM: artificial
<220> FEATURE:
<223> OTHER INFORMATION: amino acid sequence of light CDR1 (L-CDR1)

<400> SEQUENCE: 19

Arg Ala Ser Gln Asn Ile Arg Asn Ile Leu Asn
1               5                   10

<210> SEQ ID NO 20
<211> LENGTH: 7
<212> TYPE: PRT
<213> ORGANISM: artificial
<220> FEATURE:
<223> OTHER INFORMATION: amino acid sequence fo light CDR2 (L-CDR2)

<400> SEQUENCE: 20

Ala Ala Ser Asn Leu Gln Ser
1               5

<210> SEQ ID NO 21
<211> LENGTH: 9
<212> TYPE: PRT
<213> ORGANISM: artificial
<220> FEATURE:
<223> OTHER INFORMATION: amino acid sequence of light CDR3 (L-CDR3)

<400> SEQUENCE: 21

Gln Gln Ser Tyr Ser Met Pro Arg Thr
1               5

<210> SEQ ID NO 22
<211> LENGTH: 12
<212> TYPE: PRT
<213> ORGANISM: artificial
<220> FEATURE:
<223> OTHER INFORMATION: amino acid sequence of light CDR1 (L-CDR1)

<400> SEQUENCE: 22

Arg Ala Ser His Arg Val Ser Ser Asn Tyr Leu Ala
1               5                   10

<210> SEQ ID NO 23
<211> LENGTH: 7
<212> TYPE: PRT
<213> ORGANISM: artificial
<220> FEATURE:
<223> OTHER INFORMATION: amino acid sequence of light CDR2 (L-CDR2)

<400> SEQUENCE: 23

Gly Ala Ser Asn Arg Ala Thr
1               5

<210> SEQ ID NO 24
<211> LENGTH: 9
<212> TYPE: PRT
<213> ORGANISM: artificial
<220> FEATURE:

```
<223> OTHER INFORMATION: amino acid sequence of light CDR3 (L-CDR3)

<400> SEQUENCE: 24

Gln Gln Tyr Ala Ser Ser Pro Val Thr
1               5

<210> SEQ ID NO 25
<211> LENGTH: 10
<212> TYPE: PRT
<213> ORGANISM: artificial
<220> FEATURE:
<223> OTHER INFORMATION: amino acid sequence of heavy CDR3 (H-CDR3)

<400> SEQUENCE: 25

Gly Tyr Ile Phe Pro Thr Phe Ala Leu His
1               5                   10

<210> SEQ ID NO 26
<211> LENGTH: 16
<212> TYPE: PRT
<213> ORGANISM: artificial
<220> FEATURE:
<223> OTHER INFORMATION: amino acid sequence of heavy CDR2 (H-CDR2)

<400> SEQUENCE: 26

Ser Ile Asn Thr Ala Ser Gly Lys Thr Lys Phe Ser Thr Lys Phe Gln
1               5                   10                  15

<210> SEQ ID NO 27
<211> LENGTH: 13
<212> TYPE: PRT
<213> ORGANISM: artificial
<220> FEATURE:
<223> OTHER INFORMATION: amino acid sequence of heavy CDR3 (H-CDR3)

<400> SEQUENCE: 27

Asp Arg Phe Gln Asn Ile Met Ala Thr Ile Leu Asp Val
1               5                   10

<210> SEQ ID NO 28
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 28

Val Gly Ser Phe Ser Gly Ile Ala Tyr Arg Pro
1               5                   10

<210> SEQ ID NO 29
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 29

Val Gly Ser Phe Ser Gly Pro Ala Leu Arg Pro
1               5                   10

<210> SEQ ID NO 30
<211> LENGTH: 11
<212> TYPE: PRT
<213> ORGANISM: artificial
<220> FEATURE:
<223> OTHER INFORMATION: amino acid sequence of heavy CDR3 (H-CDR3)
```

```
<400> SEQUENCE: 30

Val Gly Ser Phe Ser Pro Pro Thr Tyr Gly Tyr
1               5                   10

<210> SEQ ID NO 31
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 31

Val Gly Ser Phe Ser Gly Tyr Pro Tyr Arg Pro
1               5                   10

<210> SEQ ID NO 32
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 32

Val Gly Ser Phe Ser Pro Leu Thr Leu Gly Leu
1               5                   10

<210> SEQ ID NO 33
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 33

Val Gly Ser Phe Ser Gly Pro Val Tyr Gly Leu
1               5                   10

<210> SEQ ID NO 34
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 34

Val Gly Ser Phe Ser Pro Pro Ala Tyr Arg Pro
1               5                   10

<210> SEQ ID NO 35
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 35

Val Gly Ser Phe Ser Pro Val Thr Tyr Gly Leu
1               5                   10

<210> SEQ ID NO 36
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 36
```

```
Val Gly Ser Phe Ser Gly Leu Ala Tyr Arg Pro
1               5                   10

<210> SEQ ID NO 37
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 37

Val Gly Ser Phe Ser Pro Ile Thr Tyr Gly Leu
1               5                   10

<210> SEQ ID NO 38
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 38

Val Gly Ser Phe Ser Gly Trp Ala Phe Asp Tyr
1               5                   10

<210> SEQ ID NO 39
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 39

Val Gly Ser Phe Ser Gly Trp Ala Phe Asp Tyr
1               5                   10

<210> SEQ ID NO 40
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 40

Leu Gly Ser Val Thr Ala Trp Ala Phe Asp Tyr
1               5                   10

<210> SEQ ID NO 41
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 41

Ala Gly Ser Ile Pro Gly Trp Ala Phe Asp Tyr
1               5                   10

<210> SEQ ID NO 42
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 42

Val Gly Ser Phe Ser Pro Leu Thr Met Gly Leu
1               5                   10
```

```
<210> SEQ ID NO 43
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 43

Val Gly Ser Phe Ser Pro Leu Thr Met Gly Leu
1               5                   10

<210> SEQ ID NO 44
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 44

Val Gly Ser Phe Ser Gly Pro Ala Leu His Leu
1               5                   10

<210> SEQ ID NO 45
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 45

Val Gly Ser Val Ser Arg Ile Thr Tyr Gly Phe
1               5                   10

<210> SEQ ID NO 46
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 46

Val Gly Ser Phe Ser Pro Leu Thr Leu Gly Leu
1               5                   10
```

METHOD OF TREATING PAIN USING AN ANTAGONIST OF GM-CSF

This application claims the benefit of U.S. Provisional Application No. 61/139,687, filed Dec. 22, 2008, and U.S. Provisional Application No. 61/164,491, filed Mar. 30, 2009, which are both incorporated by reference in their entireties.

FIELD OF THE INVENTION

The present invention relates generally to a method for the treatment and prophylaxis of pain. In accordance with the present invention, it is proposed that antagonists of GM-CSF are effective in the treatment of pain. Antagonists of GM-CSF include, but are not limited to, antibodies which are specific for GM-CSF or the GM-CSF receptor. The present invention further provides transgenic animals, such as a GM-CSF knock-out mouse, useful for testing antagonists in certain disease models.

BACKGROUND OF THE INVENTION

Pain

Pain of any type is the most frequent reason for physician consultation in the United States, prompting half of all Americans to seek medical care annually. It is a major symptom in many medical conditions, significantly interfering with a person's quality of life and general functioning. Diagnosis is based on characterizing pain in various ways, according to duration, intensity, type (dull, burning or stabbing), source, or location in body. Usually pain stops without treatment or responds to simple measures such as resting or taking an analgesic, and it is then called acute pain. But it may also become intractable and develop into a condition called chronic pain, in which pain is no longer considered a symptom but an illness by itself.

Pain can be classified according to many schemes and circumstances. There are two basic types of pain: acute and chronic. Acute pain occurs for brief periods of time and is associated with temporary disorders. However, it is always an alarm signal that something may be wrong. Chronic pain is continuous and recurrent. It is associated with chronic diseases and is one of their symptoms. Pain intensity not only depends on the type of stimulus that caused it, but also on the subjective perception of the pain. Despite a wide range of subjective perception, several types of pain have been classified according to:

The stimulus that caused the pain.
The pain's duration.
The features of pain (intensity, location, etc.).
Another classification system is as follows:
Gnawing pain. Continuous with constant intensity. It generally worsens with movement.
Throbbing pain. This is typical of migraine pain. It is caused by dilation and constriction of the cerebral blood vessels.
Stabbing pain. Intense and severe. It is caused by mechanical stimuli.
Burning pain. A constant, burning feeling, like, for example, the type of pain caused by heartburn.
Pressing pain. Caused by constriction of the blood vessels or muscles.
There are also specific types of pain:
Muscle pain. Also known as myalgia, this pain involves the muscles and occurs after excessive exertion or during inflammation.
Colicky pain. Caused by muscle contractions of certain organs, such as the uterus during the menstrual period. Generally cyclic in nature.
Referred pain. Occurs when the painful sensation is felt in a site other than the one where it is actually occurring, depending upon how the brain interprets information it receives from the body.
Post-surgical or Post-operative pain. Occurs after surgery and is due to lesions from surgical procedures.
Bone cancer pain. Certain types of cancers, such as prostate, breast, or other soft-tissue tumors, may progress to a painful disorder of the bone known as metastatic bone disease.

Standard Care for Pain Treatment

There are many ways to treat pain. Treatment varies depending on the cause of pain. The main treatment options are as follows:

Acetaminophen: Tylenol (Acetaminophen) is used to treat pain. Unlike several other medications for pain, Tylenol does not have anti-inflammatory effects. Often, however, in cases of chronic pain, no inflammation is at the site of the pain, and thus Tylenol may be an appropriate treatment choice. Tylenol is safe when used appropriately, but can be dangerous when used excessively. Also, Tylenol may cause unwanted effects when used with certain other medicaments.

Non-Steroidal Anti-Inflammatory Medications (NSAIDs): The NSAIDs (such as Ibuprofen, Motrin, Aleve, etc.) are most beneficial in cases of acute pain, or flare-ups in patients with chronic pain. NSAIDs are also excellent at treating inflammatory conditions including tendonitis, bursitis, and arthritis. In general, NSAID use is limited for patients with chronic pain because of concerns about the development to stomach problems. While the newer, so-called COX-2 inhibitors, such as Celebrex, were designed to avoid this complication, caution should still be used when using these medications for long periods of time.

Corticosteroids: As with NSAIDs, corticosteroids are powerful anti-inflammatory medications, and best used for acute pain or for flare-ups of a chronic inflammatory problem. Corticosteroids can either be taken orally (such as Medrol. Prednisone), or injected into the soft tissues or joints (cortisone injections).

Narcotics: Narcotics should be considered if pain cannot be otherwise controlled. Many narcotics can be dangerous and addicting. While narcotic medications are useful for acute pain, they also have significant side effects. The short-acting types of these medications can lead to overuse and the development of tolerance. Long-acting options have fewer side effects, and better control of chronic pain. Narcotics can become addictive when they are used for lengthy times without gradual reduction in the dose, or if the medications are taken for reasons other than pain.

Anti-Convulsants: Anti-convulsant medications are the category of medications that work to relieve nerve pain. These medications alter the function of the nerve and the signals that are sent to the brain. The most commonly prescribed anticonvulsant medication for nerve pain is called Neurontin (Gabapentin). Another option that has more recently emerged, specifically for the treatment of fibromyalgia, is called Lyrica (Pregabalin).

Local Anesthetics: Local anesthetics can provide temporary pain relief to an area. When used in the setting of chronic pain, local anesthetics are often applied as a topical patch to the area of pain. Lidoderm comes in a patch that is applied to the skin and decreases the sensitivity of this area.

All of the above mentioned treatment options have drawbacks, side effects, or use is limited to certain types of pain. Hence, there is still a high unmet medical need for the treatment of pain.

GM-CSF

Granulocyte macrophage colony-stimulating factor (GM-CSF) is a cytokine that functions as a white blood cell growth factor. GM-CSF stimulates stem cells to produce granulocytes (neutrophils, eosinophils, and basophils) and monocytes. Monocytes exit the circulation and migrate into tissue, whereupon they mature into macrophages. It is, thus, part of the natural immune/inflammatory cascade, by which activation of a small number of macrophages can rapidly lead to an increase in their numbers, a process crucial for fighting infection. The active form of GM-CSF is found extracellularly as a homodimer. In particular, GM-CSF has been identified as an inflammatory mediator in autoimmune disorders, like rheumatoid arthritis (RA), leading to an increased production of pro-inflammatory cytokines, chemokines and proteases and, thereby, ultimately to articular destruction.

GM-CSF is a cytokine which is involved in various processes in the human and the animal body. Also, certain diseases and pathologies, such as inflammatory diseases, were recently linked to GM-CSF, and GM-CSF was suggested as a potential point of intervention. The present invention discloses for the first time, that GM-CSF is also a valid target for the treatment of pain

SUMMARY OF THE INVENTION

The present invention, for the first time, demonstrates that GM-CSF is a valid target for the treatment of pain. This finding is new, and the prior art does not teach, suggest or provide any rational for such a point of intervention in the treatment of pain. Accordingly, the invention provides, e.g., a method for the treatment of pain in a subject, said method comprising the step of administering an effective amount of a GM-CSF antagonist to said subject.

In another aspect, the present invention contemplates a method for the prophylaxis of pain in a subject, said method comprising the step of administering an effective amount of GM-CSF antagonist to said subject.

In another aspect, the present invention is directed to a composition comprising a GM-CSF antagonist capable of antagonizing the ability of GM-CSF from activating, proliferating, inducing growth and/or survival of cells in a subject suffering from pain, or being suspected of suffering from pain, said composition further comprising one or more pharmaceutically acceptable carriers and/or diluents.

In another aspect, the present invention is directed to a composition comprising a GM-CSF antagonist useful in the treatment of pain, said composition further comprising one or more pharmaceutically acceptable carriers and/or diluents.

In particular aspects of the present invention, the GM-CSF antagonist is an antibody specific for GM-CSF.

In alternative aspects of the present invention, the GM-CSF antagonist is an antibody specific for the GM-CSF receptor.

In other aspects, the present invention is directed to the use of a GM-CSF antagonist in the preparation of a medicament in the treatment of pain.

In other aspects, the present invention provides GM-CSF antagonists for the treatment of pain.

In particular aspects of the present invention said pain is post-surgical pain. In alternative aspects of the present invention said pain is bone cancer pain. In yet alternative aspects of the present invention the GM-CSF antagonists have an analgesic effect.

In particular aspects of the present invention said pain is inflammatory pain.

In another aspect the present invention provides a genetically engineered mammal having a GM-CSF−/− genotype. In particular aspects said mammal is a mouse.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

DETAILED DESCRIPTION OF THE INVENTION

Figure 1:
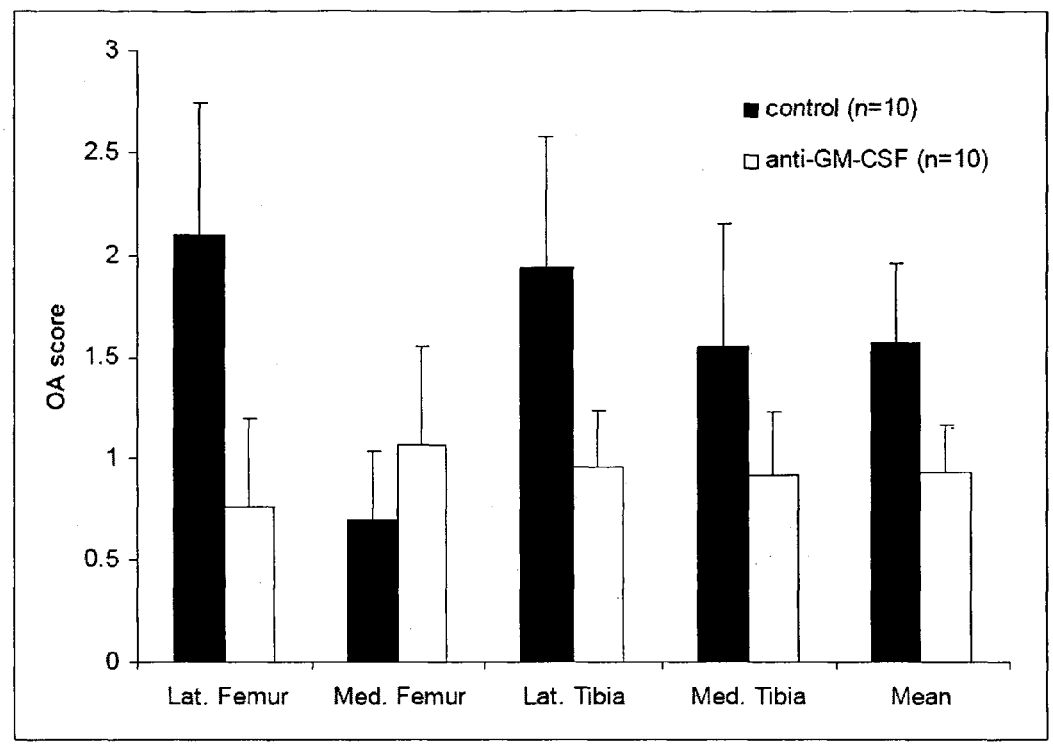
FIG. 1 shows the knee joint histology scoring of the therapeutic treatment with a GM-CSF antibody in a mouse model of OA. Lat.=Lateral. Med.=Medial. Results are expressed as mean±SEM. For all areas, except the Medial Femur, less disease was observed in mice treated with anti-GM-CSF antibody as compared to control mice.

The present invention demonstrates that GM-CSF is a valid target for the treatment of pain. In this respect, the invention provides, in one aspect, methods of using a GM-CSF antagonist to bring about a prophylactic or therapeutic benefit in the field of pain.

The present invention provides therapeutic methods comprising the administration of a therapeutically effective amount of a GM-CSF antagonist to a subject in need of such treatment. A "therapeutically effective amount" or "effective amount", as used herein, refers to the amount of a GM-CSF antagonist necessary to elicit the desired biological response. In accordance with the subject invention, the therapeutic effective amount is the amount of a GM-CSF antagonist necessary to treat and/or prevent pain.

In certain aspects the present invention provides a method for the treatment of post-surgical pain. In other aspects the present invention provides a method for the treatment of bone cancer pain. In yet other aspects the present invention provides GM-CSF antagonists which have an analgesic effect. In yet other aspects the present invention provides a method for the treatment of rheumatoid arthritis pain. GM-CSF antagonists are capable of inhibiting or blocking the pain associated with rheumatoid arthritis. In other aspects the invention provides methods for reducing incidence of rheumatoid arthritis pain, ameliorating rheumatoid arthritis pain, suppressing rheumatoid arthritis pain, palliating rheumatoid arthritis pain, and/or delaying the onset, development, or progression of rheumatoid arthritis pain in a subject, said method comprising administering an effective amount of an GM-CSF antagonist to the subject. In another aspects the present invention provides a method for preventing or treating osteoarthritis pain in an individual by administering an effective amount of an GM-CSF antagonist to the individual. In another aspect, the invention provides methods for treating inflammatory cachexia (weight loss) associated with rheumatoid arthritis in an individual comprising administering an effective amount of an GM-CSF antagonist. In another aspect, the invention provides methods for reducing incidence of osteoarthritis pain, ameliorating osteoarthritis pain, suppressing osteoarthritis pain, palliating osteoarthritis pain, and/or delaying the onset, development, or progression of osteoarthritis pain in an individual, said method comprising administering an effective amount of an GM-CSF antagonist to the individual.

"Palliating" a pain or one or more symptoms of a pain (such as rheumatoid arthritis pain or osteoarthritis pain) means lessening the extent of one or more undesirable I clinical manifestations of post-surgical pain in an individual or population of individuals treated with an GM-CSF antagonist in accordance with the invention.

In certain aspects the pain is alleviated within about 24 hours after administering GM-CSF antagonist. In other aspects, the pain is alleviated within about 4 days after administering the GM-CSF antagonist.

"GM-CSF antagonists", as used herein, includes GM-CSF antagonists in its broadest sense; any molecule which inhibits the activity or function of GM-CSF, or which by any other way exerts a therapeutic effect on GM-CSF is included. The term GM-CSF antagonists includes, but is not limited to, antibodies specifically binding to GM-CSF, inhibitory nucleic acids specific for GM-CSF or small organic molecules specific for GM-CSF. Also within the meaning of the term GM-CSF antagonist are antibodies specifically binding to the GM-CSF receptor, inhibitory nucleic acids specific for the GM-CSF receptor or small organic molecules specific for the GM-CSF receptor.

Inhibitory nucleic acids include, but are not limited to, antisense DNA, triplex-forming oligonucleotides, external guide sequences, siRNA and microRNA. Useful inhibitory nucleic acids include those that reduce the expression of RNA encoding GM-CSF by at least 20, 30, 40, 50, 60, 70, 80, 90 or 95 percent compared to controls. Inhibitory nucleic acids and methods of producing them are well known in the art siRNA design software is available.

Small organic molecules (SMOLs) specific for GM-CSF or the GM-CSF receptor may be identified via natural product screening or screening of chemical libraries. Typically the molecular weight of SMOLs is below 500 Dalton, more typically from 160 to 480 Daltons. Other typical properties of SMOLs are one or more of the following:

The partition coefficient log P is in the range from −0.4 to +5.6

The molar refractivity is from 40 to 130

The number of atoms is from 20 to 70

For reviews see Ghose et al, *J Combin. Chem:* 1:55-68, 1999 and Lipinski et al, *Adv Drug Del Rev:* 23:3-25, 1997.

Preferably, a GM-CSF antagonist for use in the present invention is an antibody specific for GM-CSF or specific for the GM-CSF receptor. Such an antibody may be of any type, such as a murine, a rat, a chimeric, a humanized or a human antibody. A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The term "chimeric antibody" or functional chimeric antibody fragment is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster.

As used herein, an antibody "binds specifically to", "specifically binds to", is "specific to/for" or "specifically recognizes" an antigen (here, GM-CSF or, alternatively, the GM-CSF receptor) if such antibody is able to discriminate between such antigen and one or more reference antigen(s), since binding specificity is not an absolute, but a relative property. The reference antigen(s) may be one or more closely related antigen(s), which are used as reference points, e.g. IL3, IL5, IL-4, IL13 or M-CSF. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions of GM-CSF or the GM-CSF receptor, or between one or more key amino acid residues or stretches of amino acid residues of GM-CSF or the GM-CSF receptor.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')₂ fragment, a Fab fragment, scFv or constructs comprising single immunoglobulin variable domains or single domain antibody polypeptides, e.g. single heavy chain variable domains or single light chain variable domains. The F(ab')₂ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved; for example, by analyzing a database of human sequences and devising a polypeptide sequence utilizing the data obtained therefrom. Methods for designing and obtaining in silico-created sequences are described, for example, in Knappik et al/, *J. Mol. Biol.* 296:57, 2000; Krebs et al, *J. Immunol. Methods.* 254:67, 2001, Rothe et al, *J. Mol. Biol.* 376:1182, 2008 and U.S. Pat. No. 6,300,064 issued to Knappik et al 2000 supra which hereby are incorporated by reference in their entirety.

Any antibody specific for GM-CSF may be used with the present invention. Exemplary antibodies are disclosed in U.S. Ser. No. 11/914,599, which is incorporated by reference in its entirety. Other exemplary antibodies include antibodies comprising an amino acid sequence of a heavy chain variable region as depicted in SEQ ID NO:1 or an amino acid sequence of a light chain variable region as depicted in SEQ ID NO:2. Yet other exemplary antibodies include antibodies which are derived from antibodies comprising a heavy chain variable region as depicted in SEQ ID NO:1 or an amino acid sequence of a light chain variable region as depicted in SEQ ID NO:2. Yet other exemplary antibodies include antibodies which have the same specificity and/or bind to the same epitope as antibodies comprising a heavy chain variable region as depicted in SEQ ID NO:1 or an amino acid sequence of a light chain variable region as depicted in SEQ ID NO:2. Yet other exemplary antibodies include antibodies which comprise a heavy chain variable region which is at least 70%, at least 80%, at least 90% or at least 95% homologous to the sequence depicted in SEQ ID NO:1. Yet other exemplary antibodies include antibodies which comprise a light chain variable region which is at least 70%, at least 80%, at least 90% or at least 95% homologous to the sequence depicted in SEQ ID NO.:2.

```
SEQ ID NO. 1:
Met Glu Leu Ile Met Leu Phe Leu Leu Ser Gly Thr

Ala Gly Val His Ser Glu Val Gln Leu Gln Gln Ser

Gly Pro Glu Leu Val Lys Pro Gly Ala Ser Val Lys

Ile Ser Cys Lys Ala Ser Gly Tyr Thr Phe Thr Asp

Tyr Asn Ile His Trp Val Lys Gln Ser His Gly Lys

Ser Leu Asp Trp Ile Gly Tyr Ile Ala Pro Tyr Ser

Gly Gly Thr Gly Tyr Asn Gln Glu Phe Lys Asn Arg

Ala Thr Leu Thr Val Asp Lys Ser Ser Ser Thr Ala

Tyr Met Glu Leu Arg Ser Leu Thr Ser Asp Asp Ser

Ala Val Tyr Tyr Cys Ala Arg Arg Asp Arg Phe Pro

Tyr Tyr Phe Asp Tyr Trp Gly Gln Gly Thr Thr Leu

Arg Val Ser Ser Val Ser Gly Ser

SEQ ID No. 2:
Met Gly Phe Lys Met Glu Ser Gln Ile Gln Val Phe

Val Tyr Met Leu Leu Trp Leu Ser Gly Val Asp Gly

Asp Ile Val Met Ile Gln Ser Gln Lys Phe Val Ser

Thr Ser Val Gly Asp Arg Val Asn Ile Thr Cys Lys

Ala Ser Gln Asn Val Gly Ser Asn Val Ala Trp Leu

Gln Gln Lys Pro Gly Gln Ser Pro Lys Thr Leu Ile

Tyr Ser Ala Ser Tyr Arg Ser Gly Arg Val Pro Asp

Arg Phe Thr Gly Ser Gly Ser Gly Thr Asp Phe Ile

Leu Thr Ile Thr Thr Val Gln Ser Glu Asp Leu Ala

Glu Tyr Phe Cys Gln Gln Phe Asn Arg Ser Pro Leu

Thr Phe Gly Ser Gly Thr Lys Leu Glu Leu Lys Arg

Ala Asp Ala Ala Pro Thr Val Ser Ile Phe Pro Pro

Ser Ser Lys Gly Glu Phe
```

Alternative exemplary antibodies that can be used in the present invention are antibodies comprising an amino acid sequence of a heavy chain variable region as depicted in SEQ ID NO:3 or an amino acid sequence of a light chain variable region as depicted in SEQ ID NO:4. Other exemplary antibodies include antibodies which are derived from antibodies comprising a heavy chain variable region as depicted in SEQ ID NO:3 or an amino acid sequence of a light chain variable region as depicted in SEQ ID NO:4. Yet other exemplary antibodies include antibodies which have the same specificity and/or bind to the same epitope as antibodies comprising a heavy chain variable region as depicted in SEQ ID NO:3 or an amino acid sequence of a light chain variable region as depicted in SEQ ID NO:4. Yet other exemplary antibodies include antibodies which comprise a heavy chain variable region which is at least 70%, at least 80%, at least 90% or at least 95% homologous to the sequence depicted in SEQ ID NO:3. Yet other exemplary antibodies include antibodies which comprise a light chain variable region which is at least 70%, at least 80%, at least 90% or at least 95% homologous to the sequence depicted in SEQ ID NO:4.

SEQ ID NO. 3:
heavy MOR
QVQLVESGGGLVQPGGSLRLSCAASGFTFSSYWMNWVRQAPGKGLEWVS

GIENKYAGGATYYAASVKGRFTISRDNSKNTLYLQMNSLRAEDTAVYYC

ARGFGTDFWGQGTLVTVSS

SEQ ID NO. 4:
light MOR
DIELTQPPSVSVAPGQTARISCSGDSIGKKYAYWYQQKPGQAPVLVIYK

KKRPSGIPERFSGSNSGNTATLTISGTQAEDEADYYCSAWGDKGMVFGG

GTKLTVLGQ

Alternative exemplary antibodies that can be used in the present invention are antibodies comprising a H-CDR3 sequence selected from:

```
                                      (SEQ ID NO. 5)
Ser Gly Leu Ile Phe Asp Tyr Trp Leu Asp,
1               5                   10

(SEQ ID NO. 6)
Ser Gly Leu Ile Ile Asp Ala Leu Ser Pro,
1               5                   10

(SEQ ID NO. 7)
Thr Ser Leu Met Ser Ile Tyr Phe Asp Tyr,
1               5                   10

(SEQ ID NO. 8)
Ser Gly Leu Leu Phe Leu Tyr Phe Asp Tyr,
1               5                   10

(SEQ ID NO. 9)
Ser Gly Leu Ile Asn Leu Gly Met His Pro,
1               5                   10

(SEQ ID NO. 10)
Ser Gly Leu Ile Phe Asp Ala Leu Arg Asp,
1               5                   10

(SEQ ID NO. 11)
Ser Gly Leu Ile Phe Asp Lys Leu Thr Ser,
1               5                   10

(SEQ ID NO. 12)
Ser Gly Leu Ile Asn Leu His Phe Asp Thr,
1               5                   10

(SEQ ID NO. 13)
Ser Thr His Phe Ser Ala Tyr Phe Asp Tyr,
1               5                   10
```

```
                                     (SEQ ID NO. 14)
Ser Gly Leu Ile Met Asp Lys Leu Asp Asn,
1               5                   10

(SEQ ID NO. 15)
Ser Gly Leu Ile Ile Asp Asn Leu Asn Pro,
1               5                   10
and (SEQ ID NO. 16)
Ser Gly Leu Ile Ala Val Tyr Phe Asp Tyr.
1               5                   10
```

Preferably, the antibodies comprising a H-CDR3 sequence selected from any one of SEQ ID NOs. 5-16, additionally comprise the following H-CDR1 sequence:

```
Asp Tyr Leu Leu His,       (SEQ ID NO. 17)
1               5
``` and/or the following H-CDR2 sequence:

```
                                     (SEQ ID NO. 18)
Trp Leu Asn Pro Tyr Ser Gly Asp Thr Asn
1               5                   10
Tyr Ala Gln Lys Phe Gln Gly,
                15
``` and/or the following L-CDR1 sequence:

```
                                     (SEQ ID NO. 19)
Arg Ala Ser Gln Asn Ile Arg Asn Ile Leu Asn,
1               5                   10
``` and/or the following L-CDR2 sequence:

```
                                     (SEQ ID NO. 20)
Ala Ala Ser Asn Leu Gln Ser,
1               5
``` and/or the following L-CDR3 sequence:

```
                                     (SEQ ID NO. 21)
Gln Gln Ser Tyr Ser Met Pro Arg Thr.
1               5
```

Alternative exemplary antibodies that can be used in the present invention are antibodies comprising the following L-CDR1 sequence:

```
                                     (SEQ ID NO. 22)
Arg Ala Ser His Arg Val Ser Ser Asn Tyr Leu Ala,
1               5                   10
``` and/or the following L-CDR2 sequence:

```
                                     (SEQ ID NO. 23)
Gly Ala Ser Asn Arg Ala Thr,
1               5
``` and/or the following L-CDR3 sequence:

```
                                     (SEQ ID NO. 24)
Gln Gln Tyr Ala Ser Ser Pro Val Thr,
1               5
``` and/or the following H-CDR1 sequence:

```
                                            (SEQ ID NO. 25)
    Gly Tyr Ile Phe Pro Thr Phe Ala Leu His,
    1                   5                   10
``` and/or the following H-CDR2 sequence:

```
                                            (SEQ ID NO. 26)
    Ser Ile Asn Thr Ala Ser Gly Lys Thr Lys
    1                   5                   10

Phe Ser Thr Lys Phe Gln,
                    15
``` and/or the following H-CDR3 sequence:

```
                                            (SEQ ID NO. 27)
    Asp Arg Phe Gln Asn Ile Met Ala Thr Ile
    1                   5                   10

Leu Asp Val.
```

Preferably said antibody comprise all the CRDs of SEQ ID NOs. 22-27.

The GM-CSF receptor is a member of the haematopoietin receptor superfamily. It is heterodimeric, consisting of an alpha and a beta subunit. The alpha subunit is highly specific for GM-CSF whereas the beta subunit is shared with other cytokine receptors, including IL3 and IL5. This is reflected in a broader tissue distribution of the beta receptor subunit. The alpha subunit, GM-CSFR α, is primarily expressed on myeloid cells and non-haematopoetic cells, such as neutrophils, macrophages, eosinophils, dendritic cells, endothelial cells and respiratory epithelial cells. Full length GM-CSFR α is a 400 amino acid type I membrane glycoprotein that belongs to the type I cytokine receptor family, and consists of a 22 amino acid signal peptide (positions 1-22), a 298 amino acid extracellular domain (positions 23-320), a transmembrane domain from positions 321-345 and a short 55 amino acid intra-cellular domain. The signal peptide is cleaved to provide the mature form of GM-CSFR α as a 378 amino acid protein. cDNA clones of the human and murine GM-CSFR α are available and, at the protein level, the receptor subunits have 36% identity. GM-CSF is able to bind with relatively low affinity to the α subunit alone (Kd 1-5 nM) but not at all to the β subunit alone. However, the presence of both α and β subunits results in a high affinity ligand-receptor complex (Kd>>100 pM). GM-CSF signalling occurs through its initial binding to the GM-CSFR α chain and then cross-linking with a larger subunit the common β chain to generate the high affinity interaction, which phosphorylates the JAK-STAT pathway.

Any antibody specific for GM-CSF receptor may be used with the present invention. Exemplary antibodies include antibodies comprising an amino acid sequence of a H-CDR3 sequence depicted in any one of SEQ ID No's.:28-46. Other exemplary antibodies include antibodies which are derived from antibodies comprising an amino acid sequence of a H-CDR3 sequence depicted in any one of SEQ ID No's.:28-46. Yet other exemplary antibodies include antibodies which have the same specificity and/or bind to the same epitope as antibodies comprising an amino acid sequence of a H-CDR3 sequence depicted in any one of SEQ ID NOs.:28-46. Yet other exemplary antibodies include antibodies which comprise a H-CDR3 sequence which is at least 70%, at least 80%, at least 90% or at least 95% homologous to the H-CDR3 sequence depicted in any one of SEQ ID NOs.:28-46.

```
SEQ ID NO: 28:
Val Gly Ser Phe Ser Gly Ile Ala Tyr Arg Pro
                    5                   10

SEQ ID NO: 29:
Val Gly Ser Phe Ser Gly Pro Ala Leu Arg Pro
                    5                   10

SEQ ID NO: 30:
Val Gly Ser Phe Ser Pro Pro Thr Tyr Gly Tyr
                    5                   10

SEQ ID NO: 31:
Val Gly Ser Phe Ser Gly Tyr Pro Tyr Arg Pro
                    5                   10

SEQ ID NO: 32:
Val Gly Ser Phe Ser Pro Leu Thr Leu Gly Leu
                    5                   10

SEQ ID NO: 33:
Val Gly Ser Phe Ser Gly Pro Val Tyr Gly Leu
                    5                   10

SEQ ID NO: 34:
Val Gly Ser Phe Ser Pro Pro Ala Tyr Arg Pro
                    5                   10

SEQ ID NO: 35:
Val Gly Ser Phe Ser Pro Val Thr Tyr Gly Leu
                    5                   10

SEQ ID NO: 36:
Val Gly Ser Phe Ser Gly Leu Ala Tyr Arg Pro
                    5                   10

SEQ ID NO: 37:
Val Gly Ser Phe Ser Pro Ile Thr Tyr Gly Leu
                    5                   10

SEQ ID NO: 38:
Val Gly Ser Phe Ser Gly Trp Ala Phe Asp Tyr
                    5                   10

SEQ ID NO: 39;
Val Gly Ser Phe Ser Gly Trp Ala Phe Asp Tyr
                    5                   10

SEQ ID NO: 40:
Leu Gly Ser Val Thr Ala Trp Ala Phe Asp Tyr
                    5                   10

SEQ ID NO: 41:
Ala Gly Ser Ile Pro Gly Trp Ala Phe Asp Tyr
                    5                   10

SEQ ID NO: 42:
Val Gly Ser Phe Ser Pro Leu Thr Met Gly Leu
                    5                   10

SEQ ID NO: 43:
Val Gly Ser Phe Ser Pro Leu Thr Met Gly Leu
                    5                   10

SEQ ID NO: 44:
Val Gly Ser Phe Ser Gly Pro Ala Leu His Leu
                    5                   10

SEQ ID NO: 45:
Val Gly Ser Val Ser Arg Ile Thr Tyr Gly Phe
                    5                   10

SEQ ID NO: 46:
Val Gly Ser Phe Ser Pro Leu Thr Leu Gly Leu
                    5                   10
```

In certain aspects, the present invention provides methods for the treatment of pain in a subject, said method comprising the step of administering a GM-CSF antagonist to said subject. "Subject", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably the subject is a primate, most preferably a human.

In certain aspect the present invention provides a composition comprising a GM-CSF antagonist capable of antagonizing the ability of GM-CSF from activating, proliferating, inducing growth and/or survival of cells in a subject suffering from pain, or being suspected of suffering from pain, said composition further comprising one or more pharmaceutically acceptable carriers and/or diluents. Anti-GM-CSF antibodies of the present invention may antagonize any of the roles of GM-CSF in pain.

In another aspect the present invention provides a method for the prophylaxis of pain in a subject, said method comprising administering a GM-CSF antagonist to said subject. "Prophylaxis" as used in this context refers to methods which aim to prevent the onset of a disease or which delay the onset of a disease.

In certain aspect the present invention provides a composition comprising a GM-CSF antagonist useful in the treatment of pain, said composition further comprising one or more pharmaceutically acceptable carriers and/or diluents.

In other aspects the present invention provides the use of a GM-CSF antagonist in the preparation of a medicament in the treatment of pain.

In other aspects the present invention provides GM-CSF antagonists for the treatment of pain.

The compositions of the present invention are preferably pharmaceutical compositions comprising a GM-CSF antagonist and a pharmaceutically acceptable carrier, diluent or excipient, for the treatment of pain. Such carriers, diluents and excipients are well known in the art, and the skilled artisan will find a formulation and a route of administration best suited to treat a subject with the GM-CSF antagonists of the present invention.

In another aspect the present invention provides a genetically engineered mammal having a GM-CSF−/− genotype. In particular aspects said mammal is a mouse. The terms "knock-out" mouse (or mammal), a mouse (or mammal) "disrupted in" a certain gene, and a mouse (or mammal) with a "−/− genotype" are used interchangeably in the present invention and are art recognized. Respective animals are deficient in a respective gene, here GM-CSF, on both alleles of the chromosome.

Example 1

Generation of a GM-CSF−/− Mouse

The generation of GM-CSF−/− mice is described in Stanley et al (1994). Proc. Natl. Acad. Sci. USA 91:5592. Briefly, chimeric mice were generated by microinjection of 129/OLA-derived ES cells (H-2b) with a disrupted GM-CSF gene into C57BL/6 (H-2b) host blastocysts. Germline transmitters of the mutated GM-CSF allele were crossed with C57BL/6 mice for 11 generations, giving GM-CSF+/− mice that were interbred to yield the GM-CSF−/−, GM-CSF+/−, and GM-CSF+/+ mice used for the experiments. GM-CSF genotype status was determined by PCR analysis of tail DNA. Animals were fed standard rodent chow and water ad libitum and were housed with same sex littermates in sawdust-lined cages. Mice of both sexes were consigned to experiments at 8 to 15 wk of age Example 2

GM-CSF Antagonists are Effective in Treating Post-Surgical Pain

A pain model is used that mimics post surgical pain to assess the efficacy of treatment with GM-CSF antagonists.

Animals:
Male Sprague Dawley rats weighting between 220-240 grams are acclimated to the animal facility for one week prior to surgery.
Surgery:
The surgery is based on the procedure described in Brennan et al, *Pain* 64:493-501, 1996. Animals are anesthetized with a 2% isoflurane in air mixture that is maintained during surgery via a nose cone. The planter surface of the right hind paw is prepared with a povidone-iodine pad, and a 1-cm central longitudinal incision is made through skin and fascia, starting 0.5 cm from the edge of the heel and extending toward the toes. Measurements are made with a ruler with the foot held in a flexed position. The plantaris muscle is elevated using curved forceps and incised longitudinally. The muscle is incised through its full depth, between the origin and insertion. Bleeding is controlled throughout surgery by pressure applied through a gauze pad. The wound is closed with two mattress sutures (5-0 ethilon black monofilament). These sutures are knotted 5-6 times, with the first knot loosely tied. The wound site is swabbed with bacitracin solution. Animals are allowed to recover and rest in clean cages for two hours or more before behavioral testing began.
Evaluation of Resting Pain:
A cumulative pain score is used to assess pain related to weight bearing. Animals are placed on a plastic mesh (grid: 8 mm2) in clear plastic cages that are elevated on a platform (h: 18") allowing inspection of the underside of their paws. After a 20 minute acclimation period, weight bearing is assessed on a scale of 0 to 2. A score of 0 is given if the paw is blanched or pressed against the mesh, indicating full weight bearing. A score of 1 is given if the paw is favored with the skin just touching the mesh, with no blanching or indentation of the skin. A score of 2 is given if the paw is held completely off the mesh. Flinching the paw is considered a 2 if the rat is still at rest. Each animal is observed for 1 minute every 5 minutes for minutes. The sum of 6 scores (0-12) obtained during ½-hour is used to assess pain in the incised foot. Frequency of scores of 2 is also calculated and used to assess the incidence of severe pain or total guarding of the paw by the animal. Each animal is tested 24 hours before surgery (baseline), and 2 h, 24 h, 48 h, and 72 h postoperatively. The results of this experiment show that the cumulative resting pain score observed in animals treated with GM-CSF antagonists is significantly reduced compared to control animals. Weight bearing is a good correlate of how willing the animal is to use the limb, and therefore is an effective measure of pain relief. Preferably, the GM-CSF antagonist is an antibody specific for GM-CSF of specific for the GM-CSF receptor. Such antibodies are injected intra peritoneal (i.p.) at various concentrations of the antibody (e.g. 0.004, 0.01, 0.02, 0.1, 0.6, and 1 mg per kilogram of animal weight) at 15 hours pre-incision. The negative control group receives no antibody but is injected i.p. with a saline solution. Fentanyl at 0.01 mg/kg is injected i.p. as a positive control 30 minutes before testing at 24 hours post-surgery. Each experiment involves 8 animals (n=8 per group) for each condition, and the control group has 56 animals. Surgery is performed and a cumulative pain score is measured as described above. Resting pain is evaluated twenty-four hours after the surgery.

GM-CSF antagonists significantly reduce resting pain after surgery when administered at 0.02 mg/kg to 1 mg/kg dosage.

In another experiment, the efficacy of GM-CSF antagonists in reducing post-surgical pain when administered post-surgically is tested. GM-CSF specific or GM-CSF receptor specific antibodies are injected intravenously (i.v.) two hours after surgery. The control group receives no antibody but was injected i.v. with a saline solution. Surgery is performed and resting pain expressed as a cumulative pain score is assessed 24 hours after surgery. Treatment with GM-CSF antagonist significantly reduces resting pain at twenty-four hours after incision when the antibody is administered 2 hours post-incision. These results demonstrated that GM-CSF antagonist effectively alleviated post-surgical pain when administered after surgery.

Evaluation of Thermal Hyperalgesia:

Thermal hyperalgesia is assessed by the rat planter test (Ugo Basile, Italy) following a modified method of Hargreaves et al. (1988). Rats are habituated to the apparatus that consisted of four individual plexiglass boxes on an elevated glass table. A mobile radiant heat source is located under the table and focused onto the hind paw. While the animal is still, but not sleeping, the button on the control box is depressed, the radiant heat source comes on and the time taken for the animal to withdraw from the heat source is automatically recorded. This paw withdrawal latency (POOL) is detected by a light detector embedded in, the radiant heat source that senses the movement of the rat paw by a change in reflectance of the radiant source. Paw Withdrawal Latencies (PWL), in seconds, were recorded: There is an automatic cut-off point of 22.5 s to prevent tissue damage. PWL are taken three to four times for both hind paws of each animal, the mean of which represent base lines for right and left hind paws. The results are presented as the ratio of score measured in the right paw (site of surgery) and the left paw. The apparatus is calibrated once (at the beginning of the study) and set to intensity of 40 to give a normal PWL of approximately 6 seconds. Each animal is tested 24 hours before surgery (baseline), and 3 h, 24 h, 48 h, and 72 h postoperatively. Thermal hyperalgesia measurements are taken after tactile allodynia measurements. The results demonstrated that treatment with GM-CSF antagonists significantly reduced post-surgical thermal hyperalgesia.

Example 3

GM-CSF Antagonists are Effective in Treating Bone Cancer Pain

GM-CSF antagonists, such as GM-CSF specific antibodies or GM-CSF receptor specific antibodies are effective in treating cancer pain associated with bone metastasis.

We use a murine bone cancer pain model to assess the efficacy of treatment with GM-CSF antagonists. This murine model of bone cancer pain is developed by intramedullary injection of osteolytic sarcoma cells into the mouse femur and the needle hole is then filled with dental amalgam to confine the tumor to bone (see Schwei et al, *J: Neuroscience* 19:10886-10897, 1999 and Luger et al, *Pain* 99:397-406, 2002). Experiments are performed on adult male C3H/HeJ mice. On day 0, an arthrotomy is performed following induction of general anesthesia with sodium pentobarbital (50 mg/kg, intraperitoneal (i.p.)). A needle is inserted into the medullary canal to create a pathway for the sarcoma cells. A depression is then made using a pneumatic dental high speed handpiece. In addition to naive animals (n=5), sham animals (n=5) are generated with an injection of a minimum essential, media (20 µl, Sigma, St. Louis, Mo.) into the intramedullary space of the femur (designated sham) whereas sarcoma animals (n=5 for each condition tested) are injected with media containing 105 2472 osteolytic sarcoma cells (designated sarcoma or sarc) (20 µl, ATCC, Rockville, Md.). For all animals, the injection site is sealed with a dental amalgam plug to confine the cells or injected media within the intramedullary canal and followed by irrigation with sterile water (hypotonic solution). Finally, incision closure is achieved with wound clips. Clips are removed at day 5 so as not to interfere with behavioral testing. A second group of sarcoma-injected animals is treated with GM-CSF specific or GM-CSF receptor specific antibodies (e.g. 10 mg/kg, i.p.) on days 6 and 13.

Behavioral Analysis:

Animals are tested for pain-related behaviors on day 10 and day 14 post-tumor implantation. Animals are behaviorally tested using the following tests: ongoing pain (spontaneous guarding and flinching), ambulatory pain (limb use and rotarod), and movement-evoked pain (palpation-evoked guarding and palpation-evoked flinching). Animals are placed in a clear plastic observation box with a wire mesh floor and are allowed to habituate for a period of 30 min. After acclimation, spontaneous guarding, spontaneous flinching, limb use during normal ambulation in an open field, and guarding during forced ambulation is assessed. Palpation-induced guarding and flinching are measured after the 2 min period of normally non-noxious palpation of the distal femur in sarcoma- and sham-injected animals.

The number of spontaneous flinches and time to spent guarding, representative of nociceptive behavior, are recorded simultaneously during a 2-min observation period. Guarding is defined as the time the hindpaw is held aloft while ambulatory and flinches are the number of times the animal held the limb aloft. Normal limb use during spontaneous ambulation is scored on a scale of 5 to 0: (5) normal use, and (0) complete lack of limb use.

Forced ambulatory guarding is determined using a rotarod (Columbus Instruments, Columbus, Ohio). The rotated machine has a revolving rod and is equipped with speed, acceleration, and sensitivity controls. The animals are placed on the rod with ×4 speed, 8.0 acceleration, and 2.5 sensitivity. Forced ambulatory guarding is rated on a scale of 5-0: (5) normal use, and (0) complete lack of use. After a normally non-noxious palpation of the distal femur in animals every second for 2 min, the animals are placed in the observation box and their palpation-induced guarding and palpation-induced flinching is measured for an additional 2 min.

Treatment with GM-CSF Antagonists:

On day 6 and day 13, sarcoma-injected animals are intraperitoneally (i.p.) injected with GM-CSF antagonists, such as an anti-GM-CSF or an anti-GM-CSF receptor antibody (n=5), or sarcoma- and sham-injected animals were injected (i.p.) with saline (n=5 for each condition). All animals are behaviorally analyzed on days 10 and 14.

Evaluation of Ongoing Pain Behaviors:

Sarcoma-injected animals (administered with saline) develop statistically significant ongoing pain behaviors, as assessed by spontaneous guarding and spontaneous, as compared to sham injected animals (administered with saline).

Administration of GM-CSF antagonists significantly reduce spontaneous guarding and spontaneous flinching in sarcoma-injected mice on day 10 and day 14 post-sarcoma implantation as compared to administration of saline to sarcoma-injected mice. These results indicate that GM-CSF antagonists reduce ongoing pain in sarcoma-injected mice.

Evaluation of Ambulator Pain Behaviors:

Sarcoma-injected animals (administered with saline) develop ambulatory pain behaviors as assessed by limb use and forced ambulation guarding (rotarod), as compared to sham-injected animals (administered with saline). Administration of GM-CSF antagonists significantly increases limb use score and forced ambulatory guarding score in sarcoma-injected mice on day 10- and day 14 post-sarcoma implantation, as compared to administration of saline to sarcoma-injected mice. These results indicate that GM-CSF antagonists reduce ambulatory pain in sarcoma-injected mice.

Evaluation of Touch-Evoked Pain Behaviors:

Sarcoma injected animals (administered with saline) develop touch-evoked pain behaviors as assessed by palpation-induced guarding and palpation-induced flinching, as compared to sham-injected animals (administered with saline). Administration of GM-CSF antagonists significantly reduces palpation-induced guarding and palpation-induced flinching in sarcoma-injected mice on day 10 and day 14 post-sarcoma implantation as compared to administration of saline to sarcoma-injected mice. These results indicate that GM-CSF antagonists reduce touch-evoked pain in sarcoma-injected mice.

Example 4

Analgesic Effects of GM-CSF Antagonists

The analgesic effects of GM-CSF antagonists in complete Freund's adjuvant (CFA)-induced chronic arthritis in rats is investigated using the vocalization test, in comparison with indomethacine used as reference substance.

Fifty (50) male Lewis rats (LEWIS LEW/Crl Ico) weighing 150 g to 220 g at the beginning of the experimental phase are included in this study. All animals are kept for at least 5 days before the experiment, and are housed in a temperature (19.5-24.5° C.), relative humidity (45-65%) and 12-h light/dark cycle controlled room with ad libitum access to filtered tap-water and standard pelleted laboratory chow throughout the study. Animals are individually identified on the tail.

On day 0 (D0), arthritis is induced in rats by intradermal injection into the tail of 0.05 ml of a *Mycobacterium butyricum* suspension In mineral oil (10 mg/ml). On day 14 (D14), arthritic rats are included in the study according to their ability to vocalize upon gentle flexion of the hindpaw and by their arthritis index, evaluated using an inflammation score for each hind and forepaw (see Kuzuna et al, *Chem. Pharm. Bull.* (*Tokyo*) 23:1184-1191, 1975 and Pearson et al, *Arthritis Rheum.* 2:440-459, 1959).

Animals are scored based on the following criteria: Score 0: normal aspect; Score 1: erythema; Score 2: erythema with slight edema; Score 3: strong inflammation without ankylosis; Score 4: ankylosis. Only animals able to vocalize upon gentle flexion and presenting a score of 2 or 3 are included in the study.

Four groups of 10 rats each are included in the study. For group 1 (vehicle), on day 14 (D14), after selection, rats are intravenously administered by vehicle (saline). On day 18 (D18), the nociceptive intensity is evaluated by gentle flexion of the hindpaw and the intensity of the level of vocalization is recorded for each animal. For group 2 (4 days), on D 14, after selection, rats are intravenously administered GM-CSF-specific antibody. On day 18 (D18), the nociceptive intensity is evaluated by gentle flexion of the hindpaw and the intensity of the level of vocalization is recorded for each animal. For group 3 (24 hours), on day 17 after injection of CFA, rats are intravenously administered GM-CSF-specific antibody or GM-CSF receptor-specific antibody. The nociceptive intensity is evaluated by gentle flexion of the hindpaw 24 hours later, and the intensity of the level of vocalization is recorded for each animal. For group 4 (indomethacin), on day 18 (D18), the nociceptive intensity is evaluated by gentle flexion of the hindpaw one hour after oral administration of indomethacin (10 mg/kg). The intensity of the level of vocalization is also recorded for each animal. The test substances are administered in a blind and random manner by intravenous route under a volume of 5 ml/kg, whereas indomethacin was administered by oral route under a volume of 10 ml/kg.

GM-CSF antagonists show an significant analgesic effects. Statistical significance between the treated groups and the vehicle group are determined with a Dunnett's test using the residual variance after a one-way analysis of variance. GM-CSF-specific antibody and GM-CSF receptor-specific antibody significantly reduces pain in a rat model of rheumatoid arthritis 24 hours or 4 days after a single administration of the antibody.

Example 5

GM-CSF Antagonists are Effective in Treating Osteoarthritic Pain

In this experiment we used a monoclonal antibody specific for GM-CSF to demonstrate that a GM-CSF antagonist can be effective to treat osteoarthritic pain.

Collagen-Induced OA Mouse Model:

C57BL/6 mice were given 1 unit of collagenase type VII intra-articularly into the right knee on days 0 and 2 to induce joint instability (see Blom et al. (2004) Osteoarthritis Cartilage. 12; 627-35).

Anti-GM-CSF Antibody Treatment:

20 mice were randomly divided into 2 groups (10 mice/group).

Group 1 (n=10): anti-GM-CSF antibody (22E9)

Group 2 (n=10): IgG2a isotype control antibody.

Mice were treated intraperitoneally, three times per week for 6 weeks with 250 µg/mouse/treatment anti-GM-CSF antibody (22E9) or IgG2a isotype control antibody. Treatment started 4 days before the induction of OA (prophylactic), i.e. mice were treated on day −4, day −2, day 0 (the day of the first collagenase injection), then 3 times per week until the end of the experiment at 6 weeks). At weeks 2, 4 and 6, mice were bled. Both, the control antibody and the anti-GM-CSF antibody were purified to contain less than 10 Endotoxin Units/ml.

The antibody 22E9 was used as an exemplary anti-GM-CSF antibody. 22E9, which is of IgG2a isotype, is a rat anti-mouse GM-CSF-specific antibody. 22E9 was purchased from AbD Serotec (Martinsried, Germany; Cat. No. 1023501). Alternative suppliers exist, e.g. eBioscience (SanDiego, Calif., USA, Cat. No. 14-7331).

Histology:

6-weeks post final injections, histology was performed on the mice knee joints. The knee joints were collected, fixed, de-calcified, embedded in paraffin and cut at 7 µm with a microtome. Slides were stained with Safranin-O/Fast Green and Haematoxylin and Eosin to demonstrate joint pathology. Pathology investigated included: cartilage damage, synovitis, osteophyte formation and joint deformation.

The scoring system used for cartilage pathology was as follows:

Grade
0 Normal
1 Irregular but intact
1.5 Irregular with rough surface
2 Superficial fibrillation
2.5 Superficial fibrillation with reduced cells in cartilage layer
3 Vertical fissures
3.5 Branching and/or horizontal assures, tidemark ruptures
4 Cartilage loss not extending to the tide mark 4.5 Cartilage loss extending to the tide mark
5 Cartilage loss beyond the tide mark but not extending to the bone
5.5 Cartilage loss extending to the bone
6 Bone loss/remodeling/deformation
Stage
1 <10% area damaged
2 10-25% area damaged
3 25-50% area damaged
4 50-75% area damaged The grade was multiplied by the stage to give the score.

This scoring system is based on a recognized method to assess OA histopathology in clinical and experimental OA. See Pritzker et al. (2006) Osteoarthritis Cartilage; 14; 13-29. Grade is defined as OA depth progression into cartilage. Stage is defined as the horizontal extent of cartilage involvement, i.e. how much of the cartilage is affected. Grade is multiplied by the stage to give the score to give an overall score, so as to represent a combined assessment of OA severity and extent. Up to six sections are scored per mouse.

Grade was multiplied by the stage to give the score.

The following scoring system was used for synovitis (Synovial layer scoring system):

0 No changes compared to normal joints
1 Thickening of the synovial lining and some influx of inflammatory cells
2 Thickening of the synovial lining and intermediate influx of inflammatory cells
3 Profound thickening of the synovial lining and maximal observed influx of inflammatory cells Pain Measurements:

An indicator of pain used for OA models is differential distribution of weight measured using an Incapacitance Meter. This instrument measures changes in weight distribution between the operated and contralateral, unoperated hind limb. Mice were allowed to acclimatize to the equipment on three occasions prior to the experiment. Weight placed on each hind limb was measured over a 5 second period. Three separate measurements taken per mouse for each time point then averaged. Measurements were performed 2 times per week throughout the experiment. Results are expressed as collagenase injected limb/control limb×100.

Results:

For all areas analyzed in histology (except the Medial Femur), i.e. the Lateral Femur, the Lateral Tibia, and the Medial Tibia, there was a clear trend towards less disease in mice treated with anti-GM-CSF antibody. Results are depicted in FIG. 1.

Figure 2:
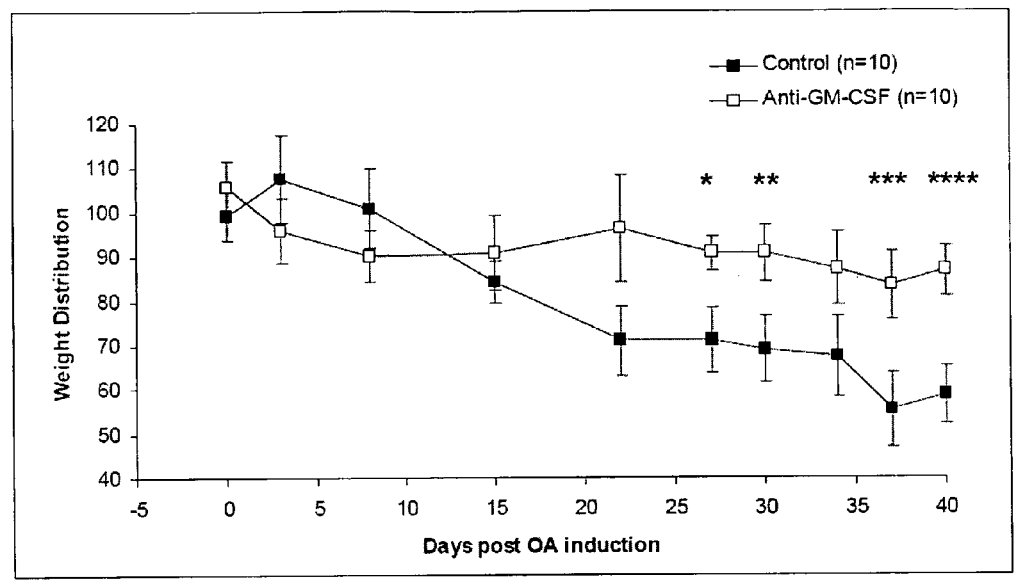
FIG. 2 shows the result of an experiment assessing the hind limb weight distribution in an incapacitance meter. Data are significant (unpaired t-test) from day 27 post OA induction onwards, as indicated in the graph.

Assessment of the weight distribution, as a measure of pain associated with the arthritis, showed a significant shift in weight away from the arthritic knee from day 27 onwards in the anti-GM-CSF mAb-treated group compared to the control mAb-treated group. Results are depicted in FIG. 2.

Mice treated with a GM-CSF antagonist showed less disease as compared to mice treated with the control antibody. Mice treated with the GM-CSF antagonist also showed significantly less pain in the latter stages of disease compared to mice treated, with the control antibody. Mice treated with the isotype control antibody showed significant increased signs of osteoarthritis as compared to the mice which received the GM-CSF-specific antibody. This demonstrates that GM-CSF antagonists are effective in the treatment of osteoarthritic pain.

Example 6

GM-CSF Antagonists are Effective in Treating Inflammatory Pain/mBSA Model

The following experiment demonstrates that GM-CSF antagonists are also effective in the treatment of inflammatory pain. To do so, mBSA/IL-1 monoarticular arthritis was induced in GM-CSF knock-out mice and in control mice. Pain was assessed with or without administration of indomethacin, a pain relieving substance, at various time points using an incapacitance tester.

Mice 24 male C57BL/6 mice and 24 male GM-CSF−/− mice (see Example 1) were used in four treatment groups:
Group 1: GM-CSF KO (n=12): methylated BSA/IL-1
Group 2: GM-CSF KO (n=12): methylated mBSA/IL-1+ indomethacin
Group 3: C57BL/6 wildtype (n=12): methylated BSA/IL-1
Group 4: C57BL/6 wildtype (n=12): methylated BSA/IL-1+ indomethacin Induction of Monoarticular Arthritis Monoarticular arthritis was induced by intraarticular injection of 10 µl of mBSA (20 mg/ml) in saline into the knee joint and 10 µl of saline into the contralateral knee joint. 20 µl of IL-1β (250 ng) was subcutaneously administered daily for 3 days. A response typically develops between days 4 and 7 after injection of mBSA and resolves by day 28. Incapacitance was tested on days 2, 3, 4, 5 and 7.

Indomethacin (Sigma) is a non-steroidal anti-inflammatory drug commonly used to reduce fever, pain, stiffness, and swelling. It works by inhibiting the production of prostaglandins. 1 mg/kg i.p. indomethacin was administered to groups 2 and 4 one hour before pain was assessed using a capacitance meter.

Read Out for Pain

An Incapacitance Tester (Dual Weight Averager) was used to automatically and reproducibly assess the analgesic potency by measuring the weight distribution on the two hind paws. The force exerted by each limb (measured in grams) is averaged over a user selectable period thus indicating any tendency for the animal to shift its weight from one side to another, hence providing a quantitative measurement of incapacitance.

Weight placed on each hind limb was measured over a 5 second period. 3 separate measurements taken per mouse for each time point then averaged. Results are expressed as injected limb/control limb×100. Thus a value of 100 means that equal weight is being placed on the right and the left limb. A value below 100 means less weight is being placed on the injected limb (left) compared with the control limb (right).

Results

Figure 3:
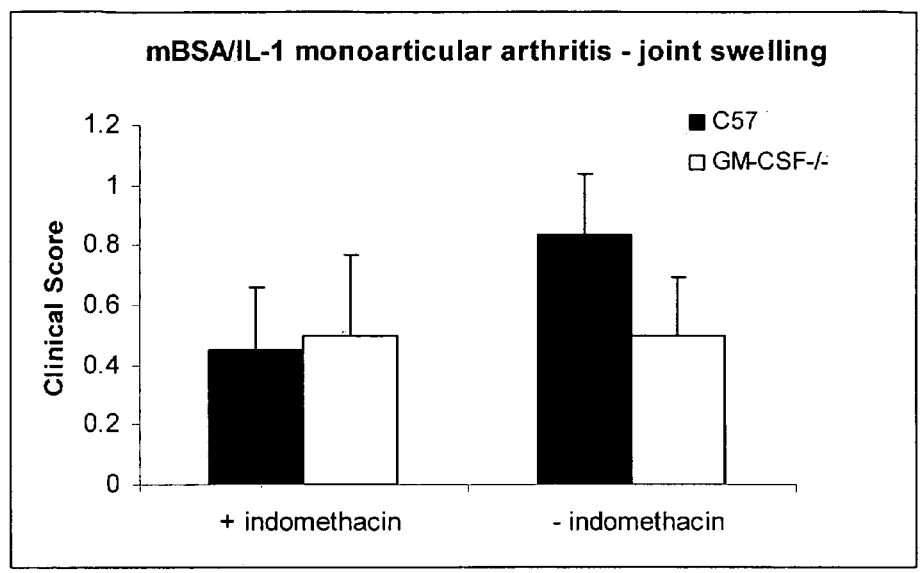
FIG. 3 shows the result of an experiment demonstrating the effectiveness of GM-CSF antagonists in the treatment of inflammatory disease (monoarticular arthritis induced by mBSA/IL1). Depicted are the clinical scores of the knee joints at day 7 following treatment. Filled bars show the results recorded for the C57BL/6 mice, open bars the results for the GM-CSF knock-out mice. Left: mice treated with indomethacin. Right: mice which did not receive treatment with indomethacin.

This model induces synovitis in the knee joint via the injection of mBSA. At day 7, the knee joints were examined visually and given a score from 0 (normal) to 3 (severely inflamed) (FIG. 3). The left knee, which was injected with mBSA, was significantly more inflamed compared with the right knee (injected with saline) (p>0.001 for C57 mice and p=0.02 for GM-CSF−/− mice) (FIG. 3). In fact, all right knees, which were injected with saline, received a score of 0. There was no significant differences between mice treated with indomethacin and those not for either strain.

Figure 4:
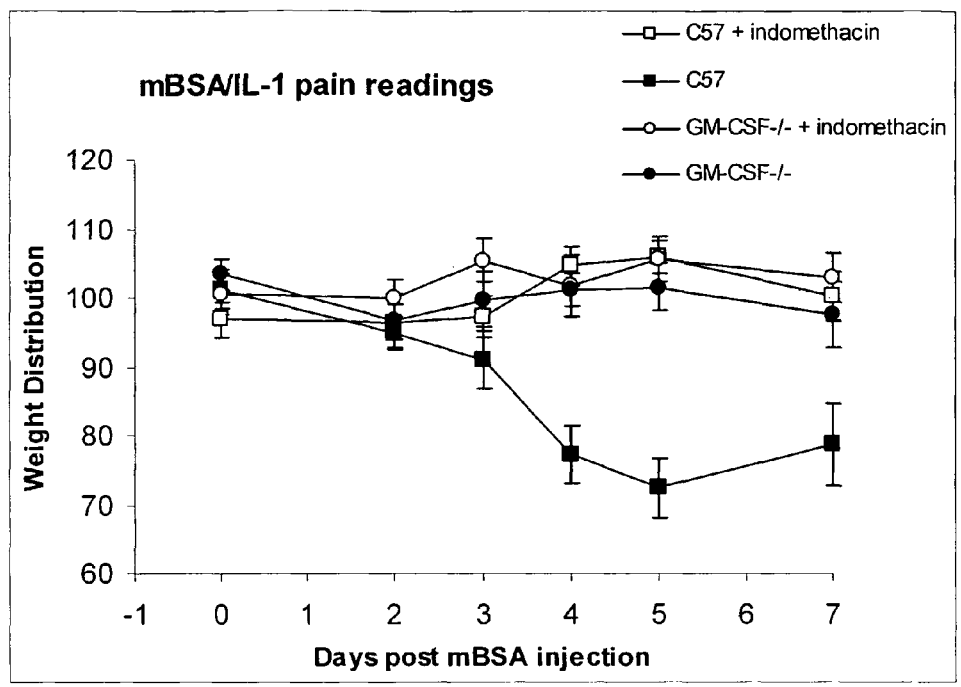
FIG. 4 shows the result of an experiment demonstrating the effectiveness of GM-CSF antagonists in the treatment of inflammatory pain (monoarticular arthritis induced by mBSA/IL1). Shown is the weight distribution measured in an incapacitance meter as a measure of pain in mice with mBSA/IL-1-induced monoarticular arthritis. Results are expressed as injected limb/control limb*100.

C57BL/6 mice showed significantly more pain (as measured by a shift in weight away from the mBSA-injected knee) compared to GM-CSF−/− mice when mBSA/IL-1 monoarticular arthritis was induced (FIG. 4). This was significant from day 4 onwards.

C57BL/6 mice treated with indomethacin showed significantly less pain compared with those mice not treated with indomethacin following mBSA/IL-1 monoarticular arthritis induction (FIG. 4), such that the readings were similar to GM-CSF−/− mice. As GM-CSF−/− did not exhibit pain, indomethacin treatment had no effect.

The significance levels are as follows:
C57BL/6 mice: indomethacin treated vs. untreated group (Group 4 vs. Group 3): day 4 p<0.0001; day 5, p<0.001; day 7, p=0.007
GM-CSF−/− mice vs. C57BL/6 mice (Group 1 vs. Group 3): day 4, p<0.0001; day 5, p<0.0001; day 7, p=0.022

These results indicate that C57BL/6 mice develop significant pain from day 4 onwards in a mBSA/IL-1 monoarticular arthritis model, whereas GM-CSF−/− mice do not show any significant signs of pain. Antagonists of GM-CSF are therefore highly effective in the treatment of inflammatory pain.

Example 7

GM-CSF Antagonists are Effective in Treating Inflammatory Pain/CFA Model

The following experiment is an additional experiment demonstrating the effectiveness of GM-CSF antagonists in the treatment of inflammatory pain. Here, inflammatory pain was induced with Complete Freund's Adjuvant. As in Experiment 5, pain was assessed with or without administration of indomethacin, a pain relieving substance, at various time points using an incapacitance meter.

Mice 12 male C57BL/6 mice and 12 male GM-CSF−/− mice (see Example 1) were used in each of the three treatment groups:
Group 1: C57BL/6 wildtype (n=12): CFA
Group 2: C57BL/6 wildtype (n=12): CFA+indomethacin
Group 3: GM-CSF KO (n=12): CFA Induction of Inflammatory Pain Complete Freund's Adjuvant (CFA) (Sigma) contains the heat-killed *Mycobacterium tuberculosis* strain, H37Ra, in mineral oil at a concentration of 1 mg/ml. CFA was mixed thoroughly by vortexing to ensure that the heat-killed bacteria are incorporated in the suspension (Kamala T (Hock immunization: a humane alternative to mouse footpad injections. J Immunol Methods 328:204-214.2007). Immediately after vortexing, the adjuvant was drawn into a glass syringe using a 19-gauge needle. Bubbles were carefully eliminated from the syringe and the needle was removed. Each mouse was injected subcutaneously in the left hind paw (footpad) with 20 μl of the CFA emulsion. 1 mg/kg i.p. indomethacin (see Experiment 5) was administered to mice of Group 2, one hour before pain assessment.

Read Out for Pain

As in Experiment 5 an Incapacitance Tester (Dual Weight Averager) was used for the automatic and reproducible assessment of analgesic potency by measuring the weight distribution on the two hind paws. Weight placed on each hind limb was measured over a 5 second period. 3 separate measurements were taken per mouse for each time point then averaged. Results are expressed as injected limb/control limb×100. Thus a value of 100 means that equal weight is being placed on the right and the left limb. A value below 100 means less weight is being placed on the injected limb (left) compared with the control limb (right). Incapacitance was tested after 24, 48 and 72 h hours post injection of CFA.

Results

Figure 5:
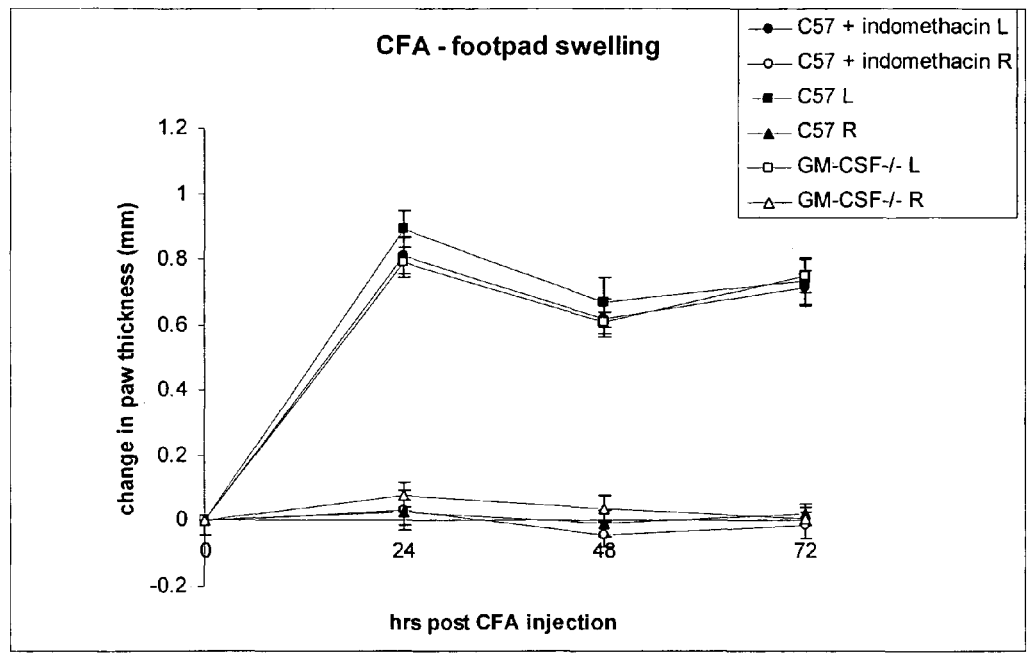
FIG. 5 shows the result of an experiment demonstrating the effectiveness of GM-CSF antagonists in the treatment of inflammatory pain. Shown is the level of inflammation as measured in the change in paw thickness following injection of CFA into the left (L) footpad. The right (R) footpad was normal. The "+ indomethacin" group was treated with indomethacin (1 mg/kg) i.p. 1 hr prior to each reading. N=12 mice/group.

Following s.c. injection of CFA into the left footpad, mice developed swelling of the left footpad, which was similar in magnitude in C57BL/6 (Group 1) and GM-CSF−/− mice (Group 3). C57BL/6 mice treated with indomethacin (Group 2) also showed no difference in the degree of swelling (see FIG. 5). There was no swelling of the contralateral (right) foot in any of the groups.

Figure 6:
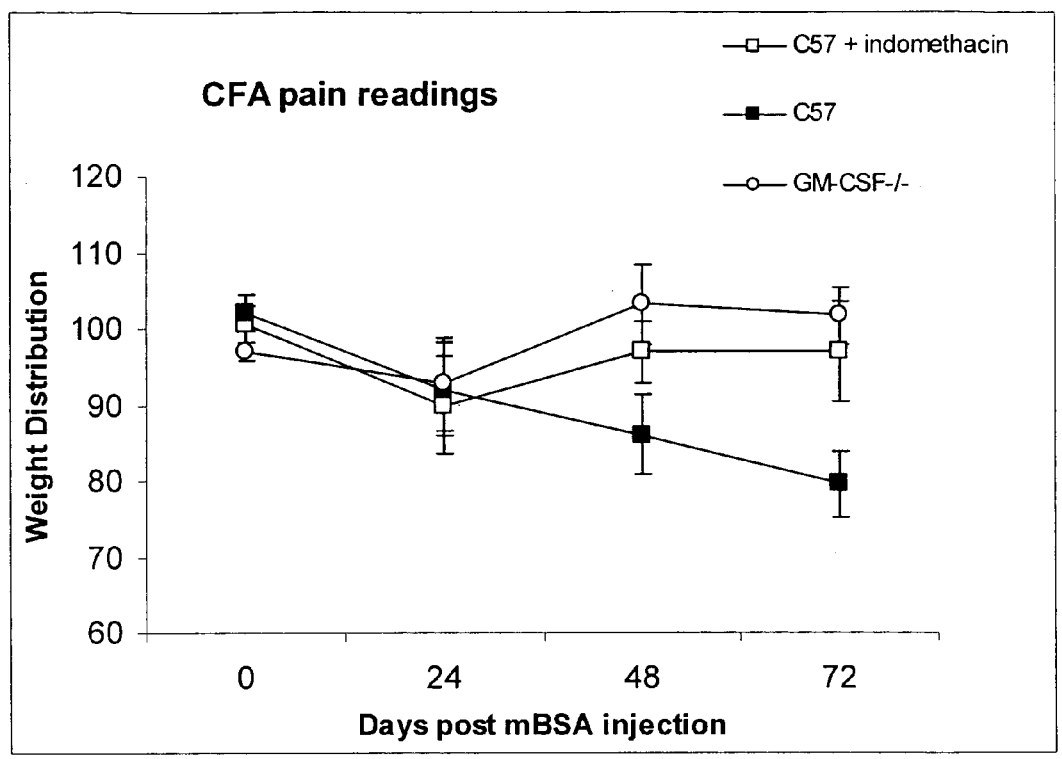
FIG. 6 shows the result of an experiment demonstrating the effectiveness of GM-CSF antagonists in the treatment of inflammatory pain. Shown is the weight distribution measured in an incapacitance meter as a measure of pain following injection of CFA into the left footpad. The right footpad was normal. The + indomethacin group was treated with indomethacin (1 mg/kg) i.p. 1 hr prior to each reading. Results are expressed as injected limb/control limb×100. N=12 mice/group.

Assessment of weight distribution, as a measure of pain, showed that C57BL/6 mice developed pain over time which was significantly greater than in GM-CSF−/− mice at 48 (p=0.03) and 72 (p=0.0009) hours post CFA injection (FIG. 6). Strikingly GM-CSF−/− mice did not develop any pain. Treatment of C57BL/6 mice with indomethacin alleviated the pain such that the readings were no different to those for GM-CSF−/− mice (FIG. 6). At 72 hrs post CFA injection C57BL/6 mice treated with indomethacin had significantly less pain than C57BL/6 mice not treated with indomethacin (p=0.05).

Summary of Significance Levels:
48 hrs:
Group 3 vs. Group 1—p=0.03,
Group 2 vs. Group 1—p=0.09,
72 hrs:
Group 3 vs. Group 1—p=0.0009,
Group 2 vs. Group 1—p=0.05, The degree of swelling of the footpad following CFA injection was no different in GM-CSF−/− mice compared with C57BL/6 mice. Furthermore, indomethacin treatment of C57BL/6 mice had no effect on swelling, which is likely due to the fact that it was only given one hour prior to the incapacitance readings. Thus the majority of swelling had already occurred before the first indomethacin injection was given at 24 hours.

In contrast, following CFA injection, C57BL/6 mice developed significant pain which was reduced by indomethacin. GM-CSF−/− mice, on the other hand, did not show any signs of pain. Hence these experiments strikingly show that although the footpads of all mice are inflamed following CFA injection, GM-CSF−/− mice do not show any signs of pain.

Example 8

Therapeutic Effectiveness of a GM-CSF Specific Antibody Comprising SEQ ID NOs. 1 or 2

Examples 2-7 are repeated, whereby as GM-CSF antagonist, a GM-CSF specific antibody comprising an amino acid sequence of a heavy chain variable region as depicted in SEQ ID No.:1 or comprising an amino acid sequence of a light chain variable region as depicted in SEQ ID No.:2 is used. Another species than mouse may be used, in particular a species to which the antibody used in this experiment is cross reactive. Preferably the animal species used in this experiment is rat.

The animals treated with the control antibody shows significant increased signs of pain as compared to the animals which received a GM-CSF specific antibody comprising an amino acid sequence of a heavy chain variable region as depicted in SEQ ID No.:1 or comprising an amino acid sequence of a light chain variable region as depicted in SEQ ID No.:2. This demonstrates the effectiveness of the antibodies in the treatment of pain.

Example 9

Therapeutic Effectiveness of a GM-CSF Specific Antibody Comprising SEQ ID NOs. 3 or 4

Examples 2-7 are repeated. As GM-CSF antagonist, a GM-CSF specific antibody comprising an amino acid sequence of a heavy chain variable region as depicted in SEQ ID NO:3 or comprising an amino acid sequence of a light chain variable region as depicted in SEQ ID NO:4 is used. Another species than mouse may be used, in particular a species to which the antibody used in this experiment is cross reactive. Preferably the animal species used in this experiment is rat.

The animals, e.g. rat, treated with the control antibody show significant increased signs of pain as compared to the animals which received a GM-CSF specific antibody comprising an amino acid sequence of a heavy chain variable region as depicted in SEQ ID NO:3 or comprising an amino acid sequence of a light chain variable region as depicted in SEQ ID NO:4. This demonstrates the effectiveness of the antibodies in the treatment of pain.

Example 10

Therapeutic Effectiveness of a GM-CSF Specific Antibodies Comprising SEQ ID NOs. 5-20

Examples 2-7 are repeated. As GM-CSF antagonist, a GM-CSF specific antibody comprising a H-CDR3 sequence selected from any one of SEQ ID NOs.5-16 is used. Preferably, said antibodies additionally comprise the H-CDR1 sequence of SEQ ID NO. 16, and/or the H-CDR2 sequence of SEQ ID NO.18, and/or the L-CDR1 sequence of SEQ ID NO:19, and/or the L-CDR2 sequence of SEQ ID NO.20), and/or the L-CDR3 sequence of SEQ ID NO.21. Another species than mouse may be used, in particular a species to which the antibody used in this experiment is cross reactive. Preferably the animal species used in this experiment is rat.

The animals, e.g. rat, treated with the control antibody show significant increased signs of pain as compared to the animals which received a GM-CSF specific antibody according to the present example. This demonstrates the effectiveness of the antibodies in the treatment of pain.

Example 11

Therapeutic Effectiveness of a GM-CSF Specific Antibodies Comprising SEQ ID NOs. 21-26

Examples 2-7 are repeated. As GM-CSF antagonist, a GM-CSF specific antibody comprising the L-CDR1 sequence of SEQ ID NO.22, and/or the L-CDR2 sequence of SEQ ID NO.23, and/or the L-CDR3 sequence of SEQ ID NO:24, and/or the H-CDR1 sequence of SEQ ID NO:25, and/or the H-CDR2 sequence of SEQ ID NO:26, and/or the H-CDR3 sequence of SEQ ID NO:27 is used. Preferably said antibody comprise all the CRDs of SEQ ID NOs.22-28. Another species than mouse may be used, in particular a species to which the antibody used in this experiment is cross reactive. Preferably the animal species used in this experiment is rat.

The animals, e.g. rat, treated with the control antibody show significant increased signs of pain as compared to the animals which received a GM-CSF specific antibody according to the present example. This demonstrates the effectiveness of the antibodies in the treatment of pain.

Example 12

Therapeutic Effectiveness of Antibodies Specific for the GM-CSF Receptor

Examples 2-7 are repeated. As GM-CSF antagonist, a GM-CSF receptor specific antibody comprising an amino acid sequence of a H-CDR3 sequence depicted in any one of SEQ ID NO's.:28-46 is used. Another species than mouse may be used, in particular a species to which the antibody used in this experiment is cross reactive. Preferably the animal species used in this experiment is rat.

The animals, e.g. rat, treated with the control antibody show significant increased signs of pain as compared to the animals which received a GM-CSF receptor specific antibody according to the present example. This demonstrates the effectiveness of the antibodies in the treatment of pain.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Brennan et al, *Pain* 64:493-501, 1996
Ghose et al, *J Combin Chem:* 1:55-68, 1999
Hargreaves et al, 1988
Knappik et al, *J. Mol. Biol.* 296:57, 2000
Krebs et al, *J. Immunol. Methods.* 254:67, 2001
Kuzuna et al, *Chem. Pharm. Bull. (Tokyo)* 23:1184-1191, 1975
Lipinski et al, *Adv Drug Del Rev:* 23:3-25, 1997
Luger et al, *Pain* 99:397-406, 2002
Pearson et al, *Arthritis Rheum.* 2:440-459, 1959
Rothe et al, *J. Mol. Biol.* 376:1182, 2008
Schwei et al, *J: Neuroscience* 19:10886-10897, 1999

The invention claimed is:

1. A method for the treatment of pain in a subject, comprising administering to the subject an antagonist of GM-CSF, wherein said antagonist is an antibody specific for GM-CSF or the GM-CSF receptor, wherein said pain is selected from bone cancer pain, osteoarthritic pain and post-surgical pain.

2. The method of claim 1, wherein said subject is a human.

3. The method of claim 1, wherein said antagonist is an antibody specific for GM-CSF.

4. The method of claim 1, wherein said antagonist is an antibody specific for the GM-CSF receptor.

5. The method of claim 1, wherein said pain is bone cancer pain.

6. The method of claim 1, wherein said pain is osteoarthritic pain.

7. The method of claim 1, wherein said pain is post-surgical pain.

* * * * *